United States Patent [19]

Kawasaki et al.

[11] Patent Number: 4,969,361
[45] Date of Patent: Nov. 13, 1990

[54] ULTRASONIC FLAW DETECTING METHOD AND APPARATUS FOR STRUCTURAL BALLS

[75] Inventors: Keiji Kawasaki, Nagoya; Koji Fushimi, Gifu; Shigeo Nishioka, Nagoya, all of Japan

[73] Assignee: NGK Insulators, Ltd., Japan

[21] Appl. No.: 311,041

[22] Filed: Feb. 16, 1989

[30] Foreign Application Priority Data

Feb. 26, 1988 [JP] Japan .................... 63-44000

[51] Int. Cl.[5] ............................................ G01M 13/04
[52] U.S. Cl. ........................................ 73/593; 73/105; 209/538
[58] Field of Search ................ 324/226, 224; 209/538, 209/598; 73/105, 593

[56] References Cited

U.S. PATENT DOCUMENTS

| | | | |
|---|---|---|---|
| 3,503,501 | 3/1970 | Seaborn | 209/538 |
| 4,551,677 | 11/1985 | Bankston | 73/37.5 |
| 4,801,020 | 1/1989 | Rogne et al. | 73/105 |

Primary Examiner—Hezron E. Williams
Assistant Examiner—Rose M. Finley
Attorney, Agent, or Firm—Arnold, White & Durkee

[57] ABSTRACT

An ultrasonic flaw detecting method able to detect defects of structural balls arranged in an ultrasonic transmitting medium with the aid of reflecting ultrasonic echoes transmitted from an ultrasonic flaw detecting probe immersed in the ultrasonic transmitting medium. The ball to be tested is arranged on two sets of ball driving rollers and the driving rollers are driven to rotate the ball during the test. An ultrasonic flaw detecting apparatus comprises ball driving rollers each including a shaft portion and a ball driving portion having a circular shape in a section perpendicular to the shaft portion to rotate the ball arranged on the ball driving rollers when the ball driving rollers are rotated, and an ultrasonic flaw detecting probe adapted to rotate about the ball for transmitting ultrasonic waves to the ball to scan defects of the ball.

10 Claims, 2 Drawing Sheets

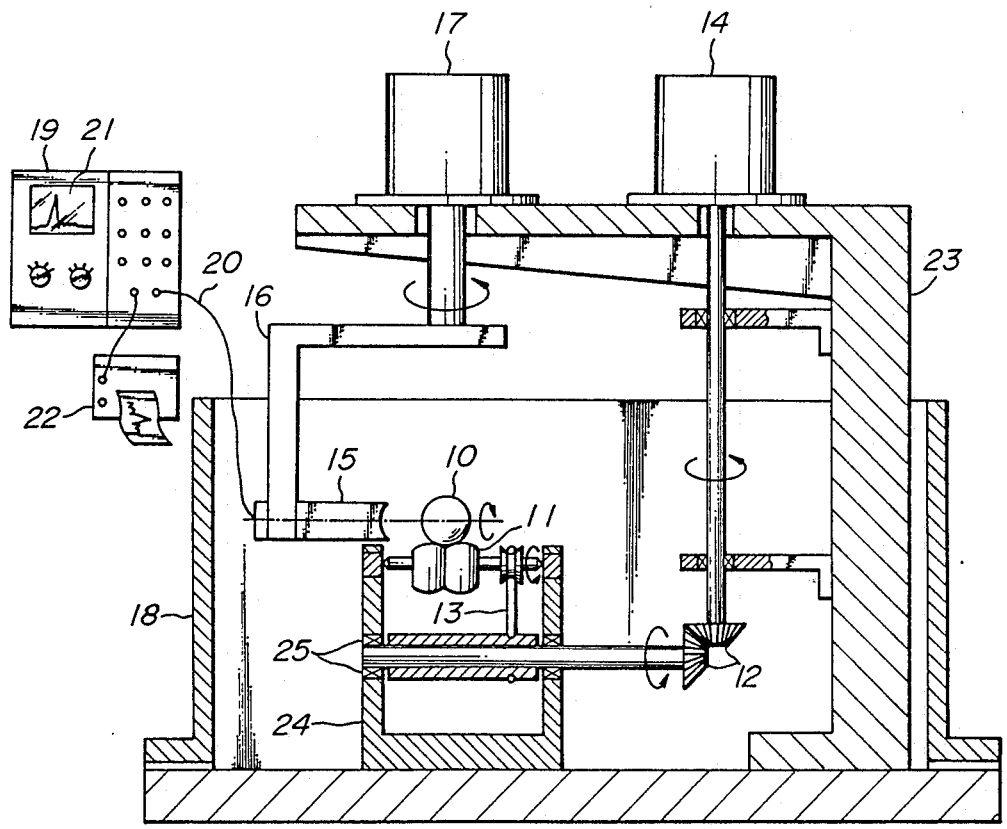
FIG_1

FIG_2
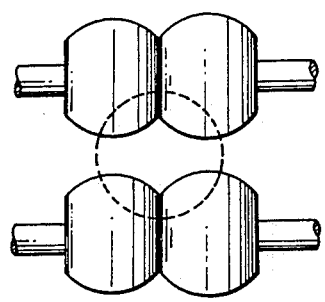
FIG_3
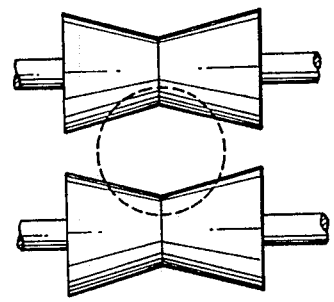
FIG_4a
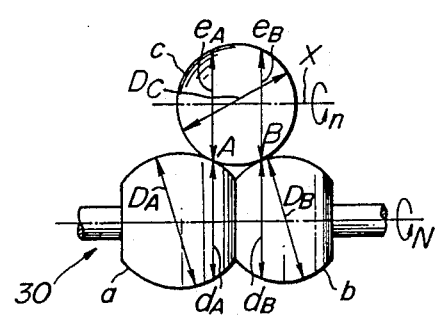
FIG_4b
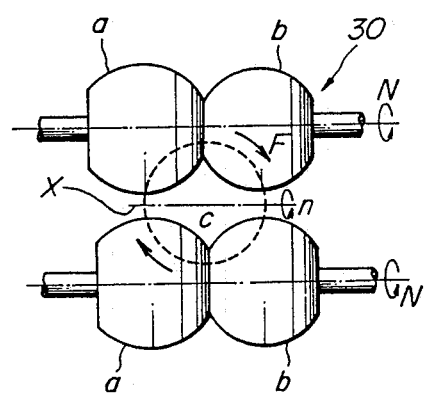

ULTRASONIC FLAW DETECTING METHOD AND APPARATUS FOR STRUCTURAL BALLS

BACKGROUND OF THE INVENTION

This invention relates to an ultrasonic flaw detecting method and apparatus for detecting defects of balls as structural members.

Surfaces and insides of balls as structural members have been inspected by an X-ray test, a cyclograph tests or appearance inspection using a microscope or the naked eye.

In the hitherto used X-ray test, cyclograph test and appearance inspection, however, structural balls to be tested have been manually rotated. Therefore, the inspections with these testing methods are time-consuming and troublesome operations and whether the balls have been scanned all over their outer circumferential surfaces cannot be confirmed.

SUMMARY OF THE INVENTION

It is a primary object of the invention to provide an improved ultrasonic flaw detecting method and apparatus for detecting defects of structural balls, which eliminate all the disadvantages of the prior art.

Inventors of this case have investigated to eliminate the disadvantages of the prior art and arrived at the present invention.

The invention relates to an ultrasonic flaw detecting method for detecting defects of balls as structural members arranged in an ultrasonic transmitting medium with the aid of reflecting ultrasonic echoes transmitted from an ultrasonic flaw detecting probe immersed in the ultrasonic transmitting medium. The method arranges a ball on two sets of ball driving rollers, the ball driving rollers being driven to rotate the ball while detecting defects of the ball.

Moreover, the ultrasonic flaw detecting apparatus for detecting defects of balls as structural members according to the invention comprises ball driving rollers each including a shaft portion and a ball driving portion having a circular shape in a section perpendicular to the shaft to rotate a ball arranged on the ball driving rollers when the ball driving rollers are rotated. The apparatus also includes an ultrasonic flaw detecting probe for transmitting ultrasonic waves to the ball to scan defects of the ball.

In a preferred embodiment of the invention, the ball driving portion of each of the ball driving rollers contact the ball at at least two points. Shapes of the ball driving portion are circular having different diameters in sections including the two points and are perpendicular to the shaft portion. With this arrangement, a center of the ball is progressively shifted during the rotation so that scanning of the ultrasonic waves is effected all over an outer circumferential surface of the ball.

As above described, the ball driving rollers are constructed by a combination of rollers each comprising a shaft portion and a ball driving portion having a circular shape in a section perpendicular to the shaft portion. The roller may be constructed by combining a shaft portion with two spherical or conical surface portions, or integrally forming the shaft portion with the two spherical or conical surface portions or combining two disc plates having curved or tapered surfaces for supporting the ball.

In more concrete examples, as shown in FIG. 2, each of two sets of rollers may be constructed by a shaft portion and two spherical surface portions having equal outer diameters. In FIG. 3, each of two sets of rollers is constructed by a shaft portion and two conical surface portions having equal outer diameters. Moreover, as shown in FIG. 4, each of two sets of rollers is constructed by a shaft portion and two spherical surface portions having different diameters.

According to the invention, a structural ball is arranged on such two sets of rollers and driven at a predetermined rotating speed by frictional forces between the ball and rotating ball driving rollers.

In the case of the ball driving rollers each comprising a shaft portion and two spherical surface portions having equal outer diameters and the two sets of rollers being driven at the same rotating speed, the ball is rotated in parallel with the rollers at a predetermined speed.

The principle of rotation of the ball driven by sets of rollers including spherical or conical surface portions having different diameters will be explained referring to FIG. 4a and 4b by way of example.

As shown in FIG. 4a and 4b, a ball c having a diameter $D_c$ is arranged on two sets of rollers each including two spherical surface portions a and b having diameters $D_A$ and $D_B$, respectively. Diameters $d_A$, $d_B$ and $e_A$ and $e_B$ of the spherical surface portions a and b and the ball c are perpendicular to a rotating axis X of the ball c and pass through contact points A and B between the ball c and the spherical surface portions a and b. When the rollers are rotated at a rotating speed N, the ball c is rotated at a rotating speed n. In this case, circumferential speeds $V_A$ and $V_B$ are as follows.

$$V_A = \pi e_A \times N/60 \times d_A/e_A = \pi N d_A/60$$

$$V_B = \pi e_B \times N/60 \times d_B/e_B = \pi N d_B/60$$

In other words, the ball c would rotate at the circumferential speeds $V_A$ and $V_B$ whose ratio are a ratio of the outer diameters $D_A$ and $D_B$ SO that the ball c is subjected to a force F resulting from a difference between the circumferential speeds $V_A$ and $V_B$. Therefore, the rotating axis of the ball c is successively shifting, while the ball c is rotating in a predetermined direction.

Balls to be tested by the ultrasonic flaw detecting method and apparatus according to the invention are ones used as structural members such as balls for bearings, wear-resistant members and sliding members.

Materials of the balls to be tested are not particularly limited. Ceramic material and metals may be used. As the ceramic materials are particularly detrimentally affected in their strength by fine defects therein, the invention is preferably applicable to balls of ceramic materials. Ceramic balls are preferably made of silicon nitride, silicon carbide, zirconia or alumina which fulfill the requirements of high strength and high hardness to be used for bearing members, wear-resistant members, sliding members and the like.

In the invention, moreover, the probe mounting portion is adapted to rotate about the ball including a center axis of rotating surface of the ball, so that the scanning of defects on and in the ball can be effected all over its outer circumferential surface without any troublesome operation.

The ultrasonic transmitting medium used in the apparatus according to the invention is generally water. However, other liquids such as turbine oil, cylinder oil and the like may be used for this purpose.

The invention will be more fully understood by referring to the following detailed specification and claims taken in connection with the appended drawings.

BRIEF DESCRIPTION OF THE DRAWINGS

FIG. 1 is an explanatory sectional view illustrating one embodiment of the ultrasonic flaw detecting apparatus according to the invention;

FIG. 2 is a plan view illustrating one embodiment of ball driving rollers used in the apparatus according to the invention;

FIG. 3 is a plan view showing another embodiment of the ball driving roller; and FIGS. 4a and 4b are side and plan views illustrating a further embodiment of the ball driving rollers.

DETAILED EXPLANATION OF THE PREFERRED EMBODIMENTS

Referring to FIG. 1, an ultrasonic flaw detecting apparatus according to the invention comprises two sets of ball driving rollers 11 each comprising two balls having a 10 mm diameter for driving a ceramic ball 10 to be tested, a ball driving motor 14 for rotating the driving rollers 11 through gears 12 and a driving belt 13, a probe mounting arm 16 for fixing a probe 15 and a probe driving motor 17 for rotating the probe 15 about the ceramic balls 10 through the probe mounting arm 16. The apparatus is arranged in a water tank 18 in which a suitable amount of water is filled. As shown in FIG. 1, the motors 14 and 17 for driving the ceramic balls 10 and the probe 15 are supported by a frame 23, and the two sets of ball driving rollers 11 are supported by a frame 24. Reference numeral 25 denotes bearings for rotatively supporting a shaft provided in a transmission between the motor 14 and two sets of ball driving rollers 11.

EXAMPLE 1

Balls 10 having 10 mm diameter made of silicon nitride were tested by the use of the apparatus as shown in FIG. 1. After one ball had been set on the ball driving rollers 11, the ball driving motor 14 for driving the balls was energized to rotate the ball driving rollers 11 through the gears 12 and the driving belt 13. In this case, the rotating speed of the ball driving motor 14 was so adjusted that the ball 10 on the ball driving rollers 11 was rotated at 300 rpm.

An ultrasonic flaw detecting probe 15 having a vibrator whose diameter was 5 mm and a focal length of 10 mm was used at a flaw detecting frequency of 30 MHz. The probe 15 was fixed to the probe mounting arm 16 and connected to an ultrasonic flaw detector 19 through a cable 20. The probe 15 was then positionally adjusted such that a distance between the probe 15 and a surface of the ball 10 was 5 mm and incident angles of ultrasonic waves were substantially perpendicular to the surfaces of the ball 10.

The ball driving motor 14 was energized to rotate the ball 10 at the rotating speed of 300 rpm, while wave forms were observed by a cathode-ray tube 21 of the ultrasonic flaw detector 19 and at the same time the wave forms were recorded on a pen-recorder 22 connected to the detector 19. Further, the probe driving motor 17 was energized to rotate the probe 15 about the ball 10 through 180° at a rotating speed of 5 rpm to scan all over the surface of the ball 10.

In the ultrasonic flaw detecting test on the ten silicon nitride balls, echoes probably caused by defects were observed on two balls. Portions of the two balls at which the echoes were observed were ground to find void defects of the order of 80-100 $\mu$m at depths 0.8 mm and 1.2 mm from the surfaces of the balls, respectively.

EXAMPLE 2

Instead of the ball driving rollers 11, two sets of ball driving rollers 30 as shown in FIGS. 4a and 4b were used. Each of sets of rollers comprises two balls having diameters of 10 mm and 12 mm, respectively. The ultrasonic flaw detecting apparatus was arranged in the water tank 18 into which the water was filled.

Silicon nitride balls 10 having a diameter of 10 mm were marked by a dry ink pen. One ball 10 was set on the ball driving rollers 30. Thereafter, the ball driving motor 14 was energized to rotate the ball driving rollers 30 through the gears 12 and the driving belt 13. In this case, the ball driving motor 14 was adjusted so that the silicon nitride ball 10 was rotated on the ball driving rollers 30 at a rotating speed of 300 rpm. A rotating center of the ball 10 was progressively shifted during such a rotation. The shifting of the center of the ball 10 was being observed by eyes with the aid of the moving mark by dry ink pen on the surface of the ball 10. Time required for rotating of the shifting through 180° was measured. As a result, it was found that the rotation shifted through 180° for 15 seconds.

An ultrasonic flaw detecting probe 15 having a vibrator 5 mm in diameter and a focal length of 10 mm was used at a flaw detecting frequency of 30 MHz. The probe 15 was fixed to the probe mounting arm 16 and connected to the ultrasonic flaw detector 19 through a cable 20. The probe 15 was then positionally adjusted such that a distance between the probe 15 and a surface of the ball 10 was 5 mm and incident angles of ultrasonic waves were substantially perpendicular to the surface of the ball 10.

The ball driving motor 14 was energized to rotate the ball 10 at the rotating speed of 300 rpm, while wave forms were observed by the cathode-ray tube 21 of the ultrasonic flaw detector 19 and at the same time the wave forms were recorded on the pen-recorder 22 connected to the detector 19. While the ball 10 was being rotated in this manner, the detection of flaws in the ball was effected for 15 seconds.

In the ultrasonic flaw detecting test on the ten silicon nitride balls, echoes probably caused by defects were observed on three balls.

As can be seen from the above description, the ultrasonic flaw detecting method and apparatus for structural balls according to the invention can rapidly and reliably detect fine defects on and in balls.

While the invention has been particularly shown and described with reference to preferred embodiments thereof, it will be understood by those skilled in the art that the foregoing and other changes in form and details can be made therein without departing from the spirit and scope of the invention.

What is claimed is:

1. A method of ultrasonically detecting defects of a ball used as a structural member, comprising the steps of:
    supporting the ball at four points thereof on two sets of ball driving rollers in an ultrasonic transmitting medium, each of said two sets of ball driving rollers including two rollers;
    driving said ball driving rollers for rotating the ball; and detecting defects of the rotating ball using reflecting ultrasonic echos transmitted from an ultrasonic flaw detecting probe immersed in said medium.

2. The method of claim 1, wherein said rollers have substantially equal diameters.

3. The method of claim 1, wherein each of said rollers of each set of said two sets of ball driving rollers has a different diameter than the other of said two rollers in said set.

4. The method of claim 1, wherein said probe is rotated about the ball around a central axis of a rotating surface of the ball.

5. An ultrasonic flaw detecting apparatus for detecting defects of a ball used as a structural member, comprising:
   two sets of ball driving rollers supporting the ball at four points thereof in an ultrasonic transmitting medium, each of said two sets of ball driving rollers including a shaft portion and two ball driving portions, said two ball driving portions having a circular cross-section in a direction perpendicular to said shaft portion, the ball being rotated when said ball driving rollers are driven; and
   an ultrasonic flaw detecting probe for transmitting ultrasonic waves to the ball to scan defects thereof.

6. The ultrasonic flaw detecting apparatus of claim 5, further comprising a probe mounting arm for supporting said probe, said probe mounting arm being rotatable about the ball around a center axis of a rotating surface of the ball.

7. The ultrasonic flaw detecting apparatus of claim 5, wherein each of said two ball driving portions of each of said two sets of ball driving rollers contacts the ball at a point such that a cross-sectional diameter taken through the contact point of one of said two ball driving portions is different than a cross-sectional diameter taken through the contact point of the other of said two ball driving portions.

8. The ultrasonic flaw detecting apparatus of claim 5, wherein said two ball driving portions of each of said two sets of ball driving rollers have substantially equal diameters.

9. The ultrasonic flaw detecting apparatus of claim 8, wherein said two ball driving portions of each of said two sets of ball driving rollers have spherical surface portions.

10. The ultrasonic flaw detecting apparatus of claim 8, wherein said two ball driving portions of each of said two sets of ball driving rollers have conical surface portions.

* * * * *